(12) United States Patent
DiLiberti et al.

(10) Patent No.: US 9,220,692 B2
(45) Date of Patent: Dec. 29, 2015

(54) METHODS OF REDUCING SYMPTOMS IN SUBJECTS USING SINGLE DOSAGE FORMS WITH TAPERING RELEASE RATES

(75) Inventors: Charles E. DiLiberti, Montclair, NJ (US); Anu Mahashabde, Kendall Park, NJ (US)

(73) Assignee: TEVA WOMEN'S HEALTH, INC., Woodcliff Lake, NJ (US)

( * ) Notice: Subject to any disclaimer, the term of this patent is extended or adjusted under 35 U.S.C. 154(b) by 482 days.

(21) Appl. No.: 13/101,929

(22) Filed: May 5, 2011

(65) Prior Publication Data

US 2011/0274740 A1 Nov. 10, 2011

Related U.S. Application Data (60) Provisional application No. 61/331,775, filed on May 5, 2010.

(51) Int. Cl.

| | | |
|---|---|---|
| *A61F 6/06* | (2006.01) | |
| *A61K 31/00* | (2006.01) | |
| *A61K 31/137* | (2006.01) | |
| *A61K 31/465* | (2006.01) | |
| *A61K 31/515* | (2006.01) | |
| *A61K 31/522* | (2006.01) | |
| *A61K 31/551* | (2006.01) | |
| *A61M 31/00* | (2006.01) | |
| *A61M 37/00* | (2006.01) | |

(52) U.S. Cl.
CPC .............. *A61K 31/00* (2013.01); *A61K 31/137* (2013.01); *A61K 31/465* (2013.01); *A61K 31/515* (2013.01); *A61K 31/522* (2013.01); *A61K 31/551* (2013.01); *A61M 31/002* (2013.01); *A61M 37/00* (2013.01)

(58) Field of Classification Search
CPC ... A61K 31/00; A61K 31/137; A61K 31/465; A61K 31/522; A61K 31/551; A61K 31/515; A61M 37/00; A61M 31/002
See application file for complete search history.

(56) References Cited

U.S. PATENT DOCUMENTS

| | | | |
|---|---|---|---|
| 4,822,616 A | 4/1989 | Zimmermann et al. | |
| 5,486,362 A * | 1/1996 | Kitchell et al. | 424/426 |
| 5,788,980 A | 8/1998 | Nabahi | |
| 6,165,497 A * | 12/2000 | Osborne et al. | 424/448 |
| 2003/0216366 A1 | 11/2003 | Leonard et al. | |
| 2010/0040671 A1* | 2/2010 | Ahmed et al. | 424/432 |
| 2011/0182977 A1* | 7/2011 | Fossel | 424/450 |

FOREIGN PATENT DOCUMENTS

| | | |
|---|---|---|
| RU | 2320331 C2 | 3/2008 |
| WO | WO 2006/026844 A1 | 3/2006 |

OTHER PUBLICATIONS

International Search Report and the Written Opinion for PCT/US2011/035402 mailed on Jul. 26, 2011.
Cutler et al., "Slow-release and injected progesterone treatments enhance acute recovery after traumatic brain injury", Pharmacology, Biochemistry and Behavior, PBB-69954, pp. 1-9, 2006.
Physician's Desk Reference 2005 "Nicoderm CQ", PDR Network LLC, Montvale, NJ.
Estring®, Physician's Leaflet, revised Aug. 2008, Pharmacia & Upjohn Company, NY, NY.
Mirena®, Patient Information Booklet, 2004, Berlex, Montville, NJ.
Norplant® System, Product Sheet, revised Aug. 2003, Wyeth Laboratories, Philadelphia, PA.
The Eurasian International Search Report for Eurasian Application No. 201290972, completed on Jul. 7, 2013.
Prilepskaya, V.N., "Hormone levonorgestrel-releasing intrauterine system," Consilium medikum, *Gynecology*, 4:1:21-28, 2002.
An English abstract translation of RU 2320331C2.

* cited by examiner

*Primary Examiner* — Suzanne Ziska
(74) *Attorney, Agent, or Firm* — Fanelli Haag PLLC (57) ABSTRACT

The present invention is directed to methods of reducing symptoms associated with an abrupt reduction in an endogenous or exogenous chemical in subjects, the methods comprising: (a) administering to the subject a single dosage form comprising an active agent, wherein the release rate of the active agent from the single dosage form tapers throughout the administration; and (b) removing the single dosage form from the subjects after the release rate of the active agent is at or below a terminal symptom threshold level.

19 Claims, 1 Drawing Sheet

METHODS OF REDUCING SYMPTOMS IN SUBJECTS USING SINGLE DOSAGE FORMS WITH TAPERING RELEASE RATES

This application claims the benefit of the filing date of U.S. Application No. 61/331,775, filed May 5, 2010, the contents of which are hereby incorporated by reference in its entirety.

BACKGROUND OF THE INVENTION

1. Field of the Invention

The present invention is directed to methods of reducing symptoms associated with an abrupt reduction in an endogenous or exogenous chemical in subjects, the methods comprising: (a) administering to the subjects a single dosage form comprising an active agent, wherein the release rate of the active agent from the single dosage form tapers throughout the administration; and (b) removing the single dosage form from the subjects after the release rate of the active agent is at or below a terminal symptom threshold level.

2. Background Art

Continual administration of an active agent often involves either a "constant dosage" regimen or a "step-down dosage" regimen. A "constant dosage" regimen requires administering an unvarying amount of an active agent at regular time intervals, e.g., in a daily dosage. For example, hormone replacement therapy often requires administering a constant daily dosage of an estrogen, thereby restoring the estrogenic hormones to their normal endogenous levels (see U.S. Pat. Nos. 5,210,081; 5,547,948; RE36,247; and see also physician's leaflet for ESTRING® (estradiol vaginal ring, Pfizer, Inc., New York, N.Y., August 2008). Hormone replacement therapy to treat menopause can be administered for a period of several months to several years.

Alternatively, for some conditions, a step-down regimen is used. A "step-down dosage" regimen requires administering an active agent in an amount that decreases over time in a step-wise or tiered manner. For example, nicotine replacement therapy is a stepdown dosage regimen indicated to reduce withdrawal symptoms, including nicotine cravings, associated with quitting smoking. For example, NICODERM CQ® (see U.S. Pat. Nos. 5,004,610; 5,342,623; 5,344,656; 5,364,630; 5,462,745; 5,508,038; 5,633,008; and 6,165,497, Glaxo SmithKline, United Kingdom) administers a once-daily dosage of nicotine for a period of 10 weeks in a decreasing series of dosage levels. During the first six weeks of the regimen, 21 mg of nicotine is administered per day, followed by two weeks of administering 14 mg of nicotine per day, and ending with administering 7 mg of nicotine per day for the final two weeks of the regimen. These doses of nicotine are not sufficient to raise the systemic circulating level of nicotine to that attained while smoking tobacco products, but are sufficient to alleviate the symptoms associated with nicotine withdrawal, and thus helps subjects in the cessation of tobacco use.

Step-down dosage regimens can also be administered to subjects in need of hormone replacement therapy. For example, see U.S. Appl. Pub. No. 2003/0216366 AI. Step-down dosage regimens are also frequently administered to subjects discontinuing the use of a barbiturate, a beta-adrenergic receptor antagonist, or an opiate. For example, withdrawal symptoms associated with addiction to heroin can be greatly reduced by administering multiple dosage forms of a long-acting opioid such as methadone (see labeling for METHADOSE®, Mallinckrodt, Hazelwood, Mo., February 2008). These regimens typically last about three to seven days, or longer, during which time the amount of methadone in each dosage is decreased in a step-down manner to alleviate the symptoms associated with heroin withdrawal. However, with both the constant dosage regimens and the step-down regimens, there are one or more periods in which there is an abrupt reduction in the amount of active agent administered. In the case of a constant regimen, the abrupt reduction in active agent occurs when the treatment period ends. In the case of the step-down regimen, the abrupt reduction in active agent occurs whenever there is a "step-down" to the next lower dosage, as well as when the treatment ends. The abrupt reduction of a regular dosage regimen of a substance can result in the development of withdrawal symptoms in a subject, and potentially, in an adverse health condition. Thus, there is a need for a single dosage form containing an active agent, and methods of administering an active agent wherein the release rate of the active agent tapers during administration that avoid such problems.

BRIEF SUMMARY OF THE INVENTION

The present invention is directed to a method of reducing a symptom associated with an abrupt reduction in an endogenous or exogenous chemical in a subject, the method comprising: (a) administering to the subject a single dosage form comprising an active agent, wherein the release rate of the active agent from the single dosage form tapers throughout the administration; and (b) removing the single dosage form from the subject after the release rate of the active agent is at or below a terminal symptom threshold level.

In some embodiments, the single dosage form IS administered vaginally, subcutaneously, intramuscularly, transdermally or buccally. In some embodiments, the single dosage form is administered to the subject for about one week to about one year. In some embodiments, the single dosage form is administered to the subject for about at least three days.

In some embodiments, the symptom is associated with menopause. In some embodiments, the active agent is a hormone. In some embodiments, the hormone is selected from the group consisting of an estrogenic compound, a progestinic compound, an androgenic compound, a corticosteroid, and combinations thereof.

In some embodiments, the symptom is associated with-drawal due to a cessation in the administration of an endogenous or exogenous chemical to the subject. In some embodiments, the active agent is selected from the group consisting of a stimulant, a beta-blocker, an opioid, an opioid antagonist, a benzodiazepine, a barbituate, and a selective serotonin reuptake inhibitor (SSRI).

In some embodiments, the symptom is associated with an addiction to an exogenous chemical. In some embodiments, the active agent is selected from the group consisting of nicotine, caffeine, and methadone.

In some embodiments, the single dosage form is selected from the group consisting of an intravaginal ring, an intrauterine dosage form, and a vaginal pessary. In some embodiments, the single dosage form is an intravaginal ring. In some embodiments, the single dosage form is an implant. In some embodiments, the single dosage form is selected from the group consisting of a transdermal adhesive patch, a transdermal reservoir dosage form, a transdermal matrix dosage form, a non-occlusive transdermal patch dosage form, a bioadhesive tablet, a bioadhesive plaster, and a buccal patch dosage form.

In some embodiments, the release rate of the active agent tapers linearly throughout the administration. In some embodiments, the release rate of the active agent tapers biphasically throughout the administration. In some embodiments, the release rate tapers first order exponentially throughout the administration.

In some embodiments the active agent is passively released from the single dosage form. In some embodiments, the active agent is actively released from the single dosage form.

The present invention is also directed to a therapeutic package comprising: (a) a single dosage form of the present invention; and (b) a label comprising directions for use of the single dosage form for reducing a symptom associated with the abrupt reduction in an endogenous or exogenous chemical in a subject, wherein the directions describe the method of reducing a symptom in a subject with anyone of the single dosage forms of the present invention.

DETAILED DESCRIPTION OF THE INVENTION

The present invention is directed to methods of reducing symptoms associated with an abrupt reduction in an endogenous or exogenous chemical in a subject, the method comprising: (a) administering to the subject a single dosage form comprising an active agent, wherein the release rate of the active agent from the single dosage form tapers throughout the administration, and (b) removing the single dosage form from the subject after the release rate of the active agent is at or below a terminal symptom threshold level.

As used herein, "symptom" refers to adverse or undesired effects associated with an abrupt reduction in an endogenous or exogenous chemical in a subject. A symptom can be an undesired physiological or psychological effect caused by a condition, disorder or disease. As used herein, "reducing a symptom" can comprise preventing the symptom, inhibiting the symptom, diminishing the symptom, alleviating the symptom, stabilizing the symptom (i.e., not worsening), delaying the onset of the symptom, slowing the progression of the symptom, reducing the likelihood of occurrence of the symptom, or eliminating the symptom.

As used herein, "abrupt reduction" refers to a decline in the systemic concentration of an endogenous or exogenous chemical in a subject over a period of time. Rates of reduction of an endogenous or exogenous chemical is specific for that chemical, and can also be dependent on the subject. As used herein, a decline in the systemic concentration of the endogenous or exogenous chemical is "abrupt" if the rate of reduction results in the occurrence of an adverse or undesired symptom in the subject. By way of example, in some embodiments, an abrupt reduction can be about 50% to about 100% reduction in the systemic concentration of an endogenous or exogenous chemical in the subject over a period of about 1 hour to about 24 hours. In some embodiments, an abrupt reduction can be about 50% to about 100% reduction in the systemic concentration of an endogenous or exogenous chemical in a subject over a period of about 1 day to about 7 days. In some embodiments, an abrupt reduction can be about 50% to about 100% reduction in the systemic concentration of an endogenous or exogenous chemical in a subject over a period of about 1 week to about 4 weeks. In some embodiments, an abrupt reduction can be about 75% to about 100% reduction in the systemic concentration of an endogenous or exogenous chemical in a subject over a period of about 1 hour to about 24 hours. In some embodiments, an abrupt reduction can be about 75% to about 100% reduction in the systemic concentration of an endogenous or exogenous chemical in a subject over a period of about 1 day to about 7 days. In some embodiments, an abrupt reduction can be about 75% to about 100% reduction in the systemic concentration of an endogenous or exogenous chemical in a subject over a period of about 1 week to about 4 weeks. In some embodiments, an abrupt reduction can be about 25% to about 75% reduction in the systemic concentration of an endogenous or exogenous chemical in a subject over a period of about 1 hour to about 24 hours. In some embodiments, an abrupt reduction can be about 25% to about 75% reduction in the systemic concentration of an endogenous or exogenous chemical in a subject over a period of about 1 day to about 7 days. In some embodiments, an abrupt reduction can be about 25% to about 75% reduction in the systemic concentration of an endogenous or exogenous chemical in a subject over a period of about 1 week to about 4 weeks. In some embodiments, an abrupt reduction can be about 25% to about 50% reduction in the systemic concentration of an endogenous or exogenous chemical in a subject over a period of about 1 hour to about 24 hours. In some embodiments, an abrupt reduction can be about 25% to about 50% reduction in the systemic concentration of an endogenous or exogenous chemical in a subject over a period of about 1 day to about 7 days. In some embodiments, an abrupt reduction can be about 25% to about 50% reduction in the systemic concentration of an endogenous or exogenous chemical in a subject over a period of about 1 week to about 4 weeks. In some embodiments, an abrupt reduction can be about 10% to about 25% reduction in the systemic concentration of an endogenous or exogenous chemical in a subject over a period of about 1 hour to about 24 hours. In some embodiments, an abrupt reduction can be about 10% to about 25% reduction in the systemic concentration of an endogenous or exogenous chemical in a subject over a period of about 1 day to about 7 days. In some embodiments, an abrupt reduction can be about 10% to about 25% reduction in the systemic concentration of an endogenous or exogenous chemical in a subject over a period of about 1 week to about 4 weeks. In some embodiments, an abrupt reduction can be about 1% to about 10% reduction in the systemic concentration of an endogenous or exogenous chemical in a subject over a period of about 1 hour to about 24 hours. In some embodiments, an abrupt reduction can be about 1% to about 10% reduction in the systemic concentration of an endogenous or exogenous chemical in a subject over a period of about 1 day to about 7 days. In some embodiments, an abrupt reduction can be about 1% to about 10% reduction in the systemic concentration of an endogenous or exogenous chemical in a subject over a period of about 1 week to about 4 weeks. In some embodiments, an abrupt reduction can be about 1% to about 25% reduction in the systemic concentration of an endogenous or exogenous chemical in a subject over a period of about 1 hour to about 24 hours. In some embodiments, an abrupt reduction can be about 1% to about 25% reduction in the systemic concentration of an endogenous or exogenous chemical in a subject over a period of about 1 day to about 7 days. In some embodiments, an abrupt reduction can be about 1% to about 25% reduction in the systemic concentration of an endogenous or exogenous chemical in a subject over a period of about 1 week to about 4 weeks. In some embodiments, an abrupt reduction can be about 5% to about 10% reduction in the systemic concentration of an endogenous or exogenous chemical in a subject over a period of about 1 hour to about 24 hours. In some embodiments, an abrupt reduction can be about 5% to about 10% reduction in the systemic concentration of an endogenous or exogenous chemical in a subject over a period of about 1 day to about 7 days. In some embodiments, the abrupt reduction results in the occurrence of a symptom.

As used herein, "endogenous chemical" refers to a chemical that is naturally present in the subject or is naturally produced in vivo by the subject. Examples of endogenous chemicals can include hormones such as estrogens, progestins, androgens, glucocorticoids, or corticosteroids. Thus, in some embodiments, the symptom is associated with a rapid hormone reduction, as experienced in menopause, or to the period of natural or induced cessation of ovarian function. Symptoms associated with menopause can also be related to peri-menopause, post menopause or oophorectomized women, or women whose endogenous sex hormone production has been suppressed by a pharmaceutical chemical composition, e.g., a GnRH agonist such as leuprolide-acetate sold under the tradename LUPRON® (TAP Pharmaceutical Products, Inc., Lake Forest, Ill.) or goserelin acetate, sold under the tradename ZOLADEX® (AstraZeneca, Wilmington, Del.).

Various symptoms associated with menopause can occur. In some embodiments, the symptom associated with menopause includes the occurrence of hot flashes. The symptom associated with menopause can also include, but is not limited to, night sweats, emotional changes (mood swings and changes in sexual interest), sleep disturbances (insomnia), premature ovarian failure, natural or induced cessation of ovarian function, or combinations thereof. Thus in some embodiments, the present invention relates to methods of reducing symptoms associated with menopause, e.g., hot flashes, the method comprising administering to a subject a single dosage form comprising estrogen, e.g., ethinyl estradiol, wherein the release rate of the active agent from the single dosage form tapers throughout the administration, and removing the single dosage form from the subject after the release rate of the active agent is at or below a terminal symptom threshold level, i.e., a level by which hot flashes would no longer occur.

In some embodiments, the symptom is due to abrupt reduction in the systemic level of an endogenous chemical, e.g., testosterone, that results from castration in a male subject.

In some embodiments, the symptom is associated withdrawal due to a cessation in the administration of an exogenous chemical to the subject. As used herein, "exogenous chemical" refers to a chemical that does not naturally occur in the subject or is not naturally produced in vivo by the subject, e.g., an exogenous chemical can include any drug, hormone, chemical or therapeutic agent administered to a subject. The symptoms can be associated with a physical addiction and/or a psychological addiction to the exogenous chemical. In some embodiments, the symptom is associated with the cessation of the administration of the exogenous chemical such as, for example, withdrawal symptoms associated with the abrupt cessation in administering an opiate, stimulant, or other chemical substance. In some embodiments, the symptom can be associated with the physical or psychological addiction to a stimulant, an opiate, a benzodiazepine, a barbiturate, or a selective serotonin reuptake inhibitor (SSRI). In some embodiments, the symptom is an adverse reaction in a subject associated with ceasing the regular administration of an exogenous chemical to which the subject has developed a tolerance. In some embodiments, the exogenous chemical can be administered by, or under the direction of, a physician. In some embodiments, the exogenous chemical is an addictive chemical. Alternatively, the exogenous chemical can be a non-addictive chemical. For example, administration of an exogenous chemical such as beta-blocker or corticosteroid may not induce an addiction to a beta-blocker or corticosteroid, however, withdrawal symptoms may result once administration of the exogenous chemical is ceased.

In some embodiments, the symptom is associated with the cessation of administration of an exogenous chemical, wherein the exogenous chemical is a stimulant. Symptoms associated with the abrupt reduction in stimulant levels in a subject can vary, are known in the art, and can include, e.g., depression, irritability, fatigue, drowsiness, insomnia, headache, loss of appetite, nausea, vomiting, muscle pain, stiffness, and combinations thereof.

In some embodiments, the symptom is associated with the cessation of administration of an exogenous chemical, wherein the exogenous chemical is a beta-blocker. Symptoms associated with the abrupt reduction in beta-blocker levels in subject can vary, are known in the art, and can include, e.g., myocardial infarction, ventricular arrhythmia, and combinations thereof.

In some embodiments, the symptom is associated with the cessation of administration of an exogenous chemical, wherein the exogenous chemical is an opioid. Symptoms associated with the abrupt reduction in opioid levels in a subject can vary, are known in the art, and can include, e.g., severe dysphoria, anxiety, eye tearing, runny nose, fevers, gastrointestinal distress, nausea, insomnia, sweating, goose bumps, cramps, deep pains, and combinations thereof.

In some embodiments, the symptom is associated with the cessation of administration of an exogenous chemical, wherein the exogenous chemical is a barbituate. Symptoms associated with the abrupt reduction in barbituate levels in a subject can vary, are known in the art, and can include, e.g., anxiety, irritability, elevated heart and/or respiration rate, muscle pain, nausea, tremors, hallucinations, confusion, seizures, and combinations thereof.

In some embodiments, the symptom is associated with the cessation of administration of an exogenous chemical, wherein the exogenous chemical is a benzodiazepine. Symptoms associated with the abrupt reduction in benzodiazipene levels in a subject can vary, are known in the art, and can include, e.g., anxiety, insomnia, depression, aggressive behavior, nausea, gastrointestinal distress, blurred vision, dizziness, ringing in the ears, headaches, muscle pain, chest pain, decreased libido, hallucinations, irregular heartbeat, and combinations thereof. In some embodiments, the symptom is associated with the cessation of administration of an exogenous chemical, wherein the exogenous chemical is a selective serotonin reuptake inhibitor (SSRI). Symptoms associated with the abrupt reduction in SSRI levels in a subject can vary, are known in the art, and can include, e.g., apathy, nausea, drowsiness, headache, bruxism, dizziness, fatigue, urinary retention, depression, suicidal ideation, photosensitivity, and combinations thereof.

As used herein, "administering" or "administration" refers to the process of transferring an amount of an active agent from a single dosage form to a subject. In some embodiments, administering means releasing an amount of active agent from a single dosage form to a subject.

Various modes of administration can be used in the present invention. For example, single dosage forms administered by the methods of the present invention can be administered intravaginally, subcutaneously, intramuscularly, transdermally, or buccally. In some embodiments, a single dosage form for use with the present invention is a monolithic intravaginal, transdermal, buccal, subcutaneous, or intramuscular single dosage form. In some embodiments, a single dosage form for use with the present invention is a multi laminate intravaginal, transdermal, buccal, subcutaneous, or intramuscular single dosage form. In some embodiments, a single dosage form for use with the present invention is a composite intravaginal, transdermal, buccal, subcutaneous, or intramuscular single dosage form. As used herein, "composite" is defined as an article that is synthesized and derives its composition and function from more than one material or compound.

"Intravaginally" refers to administration of an active agent through the vaginal, uterine, or cervical mucosa or tissue. Non-limiting examples of suitable intravaginal single dosage forms for use with the methods of the present invention includes an intravaginal ring, an intra-uterine dosage form, a vaginal pessary, and a vaginal tablet.

"Transdermally" refers to administration of an active agent across a dermal membrane. "Buccally" refers to administration of an active agent across the mucosa or tissue of the mouth. In some embodiments of the present invention, the active agent is administered via a transdermal or buccal unitary dosage form. The transdermal or buccal dosage form can be occlusive or non-occlusive. Non-limiting examples of suitable transdermal or buccal single dosage forms for use with the present invention includes a patch, an adhesive patch, a reservoir dosage form, a matrix dosage form, a multi-laminar patch, a non-occlusive patch, a bioadhesive tablet, and a bio-adhesive plaster. Transdermal and buccal single dosage forms for use with the methods of the present invention can further comprise a bio-adhesive layer useful to adhere the single dosage form to the dermis or mucosa of a subject.

"Subcutaneously" refers to administration of an active agent to tissues or blood vessels immediately below the skin. "Intramuscularly" refers to administration of an active agent through direct absorption by muscle tissues surrounding a subcutaneous single dosage form without passing through a mucosal or dermal membrane. Non-limiting examples of suitable subcutaneous or intramuscular single dosage forms for use with the methods of the present invention include implantable dosage forms.

As used herein, a "subject" refers to a human, or non-human animal, to which a single dosage form of, or for use with, the present invention is administered. In some embodiments, the subject is a domesticated animal, a herd animal, or an animal in captivity, e.g., present in a zoo, in some embodiments, the subject is a female human. In some embodiments, the subject is a male human.

As used herein, the term "single dosage form" refers to not more than one unitary dosage form being administered to a subject to reduce the symptom associated with an abrupt reduction in an endogenous or exogenous chemical in a subject. "Unitary" refers to a dosage form that consists of one part or unit. Thus, a "single dosage form" is administered to a subject in its entirety. In some embodiments, a single dosage is also removed from a subject in its entirety except for the endogenous or exogenous chemical released from the single dosage form. In some embodiments, the single dosage form does not change in size or shape during the administration.

An "active agent" refers to an endogenous or exogenous chemical that has a physiological or psychological effect on a subject. In some embodiments, the active agent can be the same as the endogenous or exogenous chemical which is abruptly reduced in the subject. In some embodiments, the active agent can be different than the endogenous or exogenous chemical which is abruptly reduced in the subject. Active agents include, but are not limited to, hormones, stimulants, beta-blockers, opioids or opiates, opioid antagonists, benzodiazepines, barbiturates, and selective serotonin reuptake inhibitors (SSRIs).

Non-limiting examples of a "hormone" include an estrogenic compound, a progestinic compound, an androgenic compound, a corticosteroid, and combinations thereof.

An "estrogenic compound" or "estrogen" refers to any of various natural or synthetic compounds that stimulate the development of female secondary sex characteristics and promote the growth and maintenance of the female reproductive system; or any other compound that mimics the physiological effect of natural estrogens, whether or not steroidal in structure. Suitable estrogenic compounds for use with the present invention include, but are not limited to, $17\alpha$-estradiol, $17\beta$-estradiol, estradiol benzoate, estradiol valerate, estradiol cypionate, estradiol heptanoate, estradiol decanoate, estradiol acetate, estradiol diacetate, 17a-ethinylestradiol, ethinylestradiol-3-acetate, ethinylestradiol-3-benzoate, estriol, estriol succinate, polyestrolphosphate, estrone, estrone acetate, estrone sulfate, diethylstilbestrol, piperazine estrone sulfate, quinestrol, mestranol, conjugated estrogens, equilin, delta-8,9-dehydro estrone, a sulfate ester of equilin, a sulfate ester of delta-8,9-dehydro estrone, and combinations thereof.

Various conjugated estrogens can also be administered from a single dosage form of, or for use with, the present invention. As used herein, the term "conjugated" refers to the sulfate ester, glucuronide ester, or mixed sulfate-glucuronide esters, of an estrogen. Estrogens also include pharmaceutically suitable salt forms of a an estrogenic compound. In some embodiments, the salt is a sodium, potassium, or 2-amino-2-(hydroxymethyl)-1,3-propanediol (Tris) salt.

Suitable conjugated estrogens for use with the present invention include, but are not limited to, sodium estrone sulfate, sodium equilin sulfate, sodium $17\alpha$-dihydroequilin sulfate, sodium $17\beta$-dihydroequilin sulfate, sodium $17\alpha$-estradiol sulfate, sodium $17\beta$-estradiol sulfate, sodium equilenin sulfate, sodium $17\alpha$-dihydroequilenin sulfate, sodium $17\beta$-dihydroequilenin sulfate or combination thereof. In some embodiments, the composition of the present invention comprises a conjugated estrogen such as, but not limited to, sodium estrone sulfate, sodium equilin sulfate, sodium $17\alpha$-dihydroequilin sulfate, sodium $17\beta$-dihydroequilin sulfate, sodium $17\alpha$-estradiol sulfate, sodium $17\beta$-estradiol sulfate, sodium equilenin sulfate, sodium $17\alpha$-dihydroequilenin sulfate, sodium $17\beta$-dihydroequilenin sulfate, $\Delta 8,9$-dehydroestrone sulfate, and combination thereof.

Non-limiting examples of suitable progestinic compounds for use with the present invention include acetoxypregnenolone, allylestrenol, anagestone acetate, chlormadinone acetate, cyproterone, cyproterone acetate, desogestrel, dihydrogesterone, dimethisterone, $17\alpha$-ethinyltestosterone, ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, trimegestone, norelgestromin, and combinations thereof.

An "androgenic compound" or "androgen" refers to any of various natural or synthetic compounds that stimulate the development of male secondary sex characteristics. Non-limiting examples of androgenic compounds for use with the present invention include the naturally occurring androgens and derivatives thereof, and the following: androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone, sodium dehydroepiandrosterone sulfate, adrenosterone 4-dihydrotestosterone, 5α-dihydrotestosterone, dromostanolone, dromostanolone propionate, methandrostenolone, testolactone, bolasterone, pregnenolone, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, ethylestrenol, danazol, stanozolol, testosterone, testosterone enanthate, testosterone propionate, testosterone cypionate, testosterone phenylacetate, testosterone acetate, testosterone isobutyrate, testosterone buciclate, testosterone heptanoate, testosterone decanoate, testosterone undecanoate testosterone caprate and testosterone isocaprate, 4-dihydrotestosterone enanthate, 4-dihydrotestosterone propionate, 4-dihydrotestosterone cypionate, 4-dihydrotestosterone phenyl acetate, 4-dihydrotestosterone acetate, 4-dihydrotestosterone isobutyrate, 4-dihydrotestosterone buciclate, 4-dihydrotestosterone heptanoate, 4-dihydrotestosterone decanoate, 4-dihydrotestosterone undecanoate, 4-dihydrotestosterone caprate, 4-dihydrotestosterone isocaprate, methyl norethandrolone, esterolone, testolactone, oxymetholone, fluoxymesterone, and combinations thereof.

A "corticosteroid" refers to any of various adrenal-cortex steroids. Non-limiting examples of corticosteroids for use with the present invention include cortisone, hydrocortisone, prednisone, methylprednisolone acetate, betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, desonide, and combinations thereof.

A "stimulant" refers to any substance that causes an increase in activity in various parts of the nervous system, or directly increases muscle activity. Non-limiting examples of stimulants for use with the present invention include nicotine, caffeine, theophylline, theobromine, amphetamine, methamphetamine, dextroamphetamine, phendimetrazine, benzphetamine, methylene-dioxymethamphetamine, phencyclidine, pemoline, diethylpropion, 3,4-methylene-dioxyamphetamine, atomoxetine, methylphenidate, dexmethylphenidate, 1-amphetamine, and combinations thereof.

A "beta-adrenergic blocking agent" or "beta-blocker" refers to a drug that opposes the excitatory effects of norepinephrine released from sympathetic nerve endings at beta-receptors. Beta-blockers can slow the heart rate, reduce blood pressure and reduce anxiety. Beta-blockers are typically used in the treatment of angina, heart arrhythmias, high blood pressure (i.e., hypertension), mitral valve prolapse, migraine and other conditions. Non-limiting examples of beta-blockers for use with the present invention include acebutolol, atenolol, betaxolol, bisoprolol, carteolol, esmolol, labetalol, metoprolol, nadolol, penbutolol, pindolol, propranolol, sotalol, timolol, and combinations thereof.

"Opioid," "opiate," or "opioid agonist" refers to any agent that binds to opioid receptors, which are found principally in the central nervous system. Non-limiting examples of opioids for use with the present invention include methadone, morphine, codeine, thebaine, diamorphine, oxycodone, hydrocodone, dihydrocodeine, hydromorphone, oxymorphone, nicomorphine, levomethadyl acetate hydrochloride, pethidine, fentanyl, alfentanil, sufentanil, remifentanil, ketobemidone, carfentanyl, propoxyphene, dextropropoxyphene, dextromoramide, bezitramide, piritramide, pentazocine, phenazocine, buprenorphine, butorphanol, nalbufine, dezocine, etorphine, tilidine, tramadol, loperamide, diphenoxylate, and combinations thereof. "Opioid antagonist" refers to an agent that binds to opioid receptors but does not activate the opioid receptors. Non-limiting examples of an opioid antagonist for use with the present invention include naloxone, naltrexone, nalmefene, and combinations thereof.

A "benzodiazepine" refers to anxiolytics that act on the central nervous system. Non-limiting examples of benzodiazepines for use with the present invention include diazepam, lorazepam, prazepam, bromazepam, clonazepam, flurazepam, oxazepam, triazolam, temazepam, midazolam, medazepam, chlordiazepoxide, alprazolam, estazolam, quazepam, clorazepate, and combinations thereof.

A "barbiturate" refers to a sedative drug related to barbituric acid. Non-limiting examples of barbiturates for use with the present invention include barbital, barbituric acid, phenobarbital, butalbital, secobarbital, aprobarbital, amobarbital, talbutal, and combinations thereof.

A "selective serotonin reuptake inhibitor" or "SSRI" refers to an antidepressant drug that blocks the neuronal uptake of serotonin, thereby resulting in increased extracellular levels of serotonin. Non-limiting examples of SSRIs for use with the present invention include citalopram, dapoxetine, escitalopram, fluvoxamine, paroxetine, sertraline, zimelidine, and combinations thereof.

As used herein, "rate," "release rate," and "rate of release" refer to the dose per unit time by which an active agent is released from a single dosage form, e.g., the release rate refers to the amount of an active agent released from the single dosage form divided by the period of time over which the releasing occurred. The units associated with rate generally correspond to an amount (i.e., moles, grams, milligrams, cubic centimeters, milliliters, etc.) per unit time (i.e., seconds, minutes, hours, days, weeks, months, years, etc.).

The release rate can be determined by numerous methods either in vivo or in vitro, as known by those in the art. For example, in vitro release rates can be determined by placing a single dosage form in a reservoir containing a solution for a first period of time and measuring a first release rate. The single dosage form is removed from the reservoir and the amount of active agent released into the solution is measured (i.e., by chromatography, spectroscopy, or some other method), giving a first rate. The single dosage form is then placed in a reservoir containing a fresh solution for a second period of time. The single dosage form is removed and the amount of active agent released into the second solution is measured to give the second rate. Similarly, the release rate of the active agent from the single dosage form can be measured in vivo, e.g., the single dosage form can be administered to a subject, and then the release rate of the active agent from the dosage form can be determined indirectly by measuring the plasma levels of the active agent over time.

While in some embodiments, the onset of administration can result in an initially increasing rate until the maximum dosage rate, i.e., the $V_{max}$, is achieved, for the methods of the present invention the maximum dosage rate occurs rapidly relative to the length of time the active agent is administered at a tapering rate. For example, in the methods of the present invention $V_{max}$ can occur within the first 10%, 5%, or 2% of the total administration time.

Figure 1:
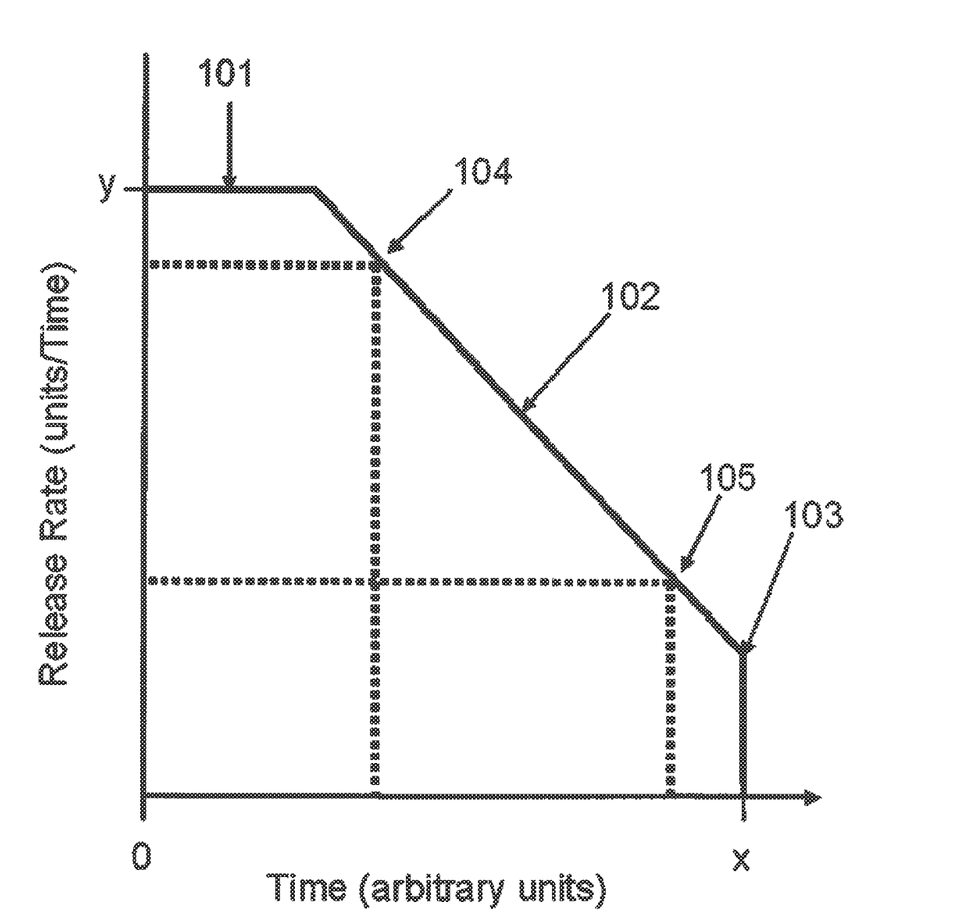
FIG. 1 is a graphical description of the release rate of an active agent from a single dosage form of the present invention. The initial release rate of the active agent, 101, can be above a symptom threshold level, 104. Once the release rate of the active agent reaches the symptom threshold level, the release rate tapers throughout the administration, 102. After the release rate of the active agent is at or below a terminal symptom threshold level, 105, the single dosage form can be removed from the subject, 103.

As used herein, the terms "tapers" and "tapering rate" refer to the general inverse trend of the release rate of the active agent from the single dosage form, i.e., the release rates of the active agent from the dosage form diminish gradually as the time of administration increases. If plotted on a graph of units of active ingredient delivered versus time, a "tapering" release rate of the present invention would produce a plot in which the rate of administering an active agent (the y-axis variable) versus time (the x-axis variable) would display a negatively sloped line or curve. In some embodiments, a statistically relevant fit of the release rate of the active agent from the dosage form measured at various times once the release rate is at or below the symptom threshold level, will produce a negatively, or tapering, sloped line or curve. In some embodiments, if plotted on a graph, a tapering release rate of the present invention would produce a plot similar to FIG. 1. In some embodiments, a statistically relevant fit of the negatively sloped portion of the plot results in a fit with a first order exponentially gradually tapering slope, i.e., a "first order exponentially tapering rate." In some embodiments, a statistically relevant fit of the negatively sloped portion of the plot results in a biphasic linear curve, i.e., a "biphasically linearly tapering rate."

In some embodiments, if plotted on a graph, a "tapering" release rate of the present invention would produce a plot in which the cumulative amount of active agent released from the single dosage form (the y-axis variable) versus time (the x-axis variable) would display a positively sloped line or curve. In some embodiments, the slope of the line gradually approaches zero.

In some embodiments, there is a correlation between the tapering release rate from the single dosage form and a reduction in the systemic level of the active agent within the subject. In some embodiments, the tapering rate does not correlate with the systemic level of active agent within the subject because of for example, the pharmacokinetics of the active agent, a first-pass metabolism of the active agent, etc., or because the active agent is delivered directly to the organs, largely or completely bypassing systemic administration.

In some embodiments, the single dosage form is administered without any breaks, discontinuities, or interruptions. In some embodiments, the administration is lacking steps or tiers. Thus, if plotted on a graph, the release rate of the present invention versus time could be fit by a single, continuous line with substantially no breaks, discontinuities, interruptions, and/or abrupt changes in the slope of the line.

In some embodiments, the release rate of the active agent from the single dosage form is initially above a symptom threshold level and tapers throughout the administration. In some embodiments, the release rate of the active agent tapers once the release rate of the active agent is at or below the symptom threshold level. As used herein, a "symptom threshold level" refers to the minimum release rate of active agent needed to reduce a symptom in a subject. Thus, if the release rate of the active agent abruptly falls below the symptom threshold level, a symptom can occur in the subject.

In some embodiments, the methods of the present invention can include discontinuing administration of the single dosage form of the present invention by removing the single dosage form from the subject after the release rate of the active agent is at or below a terminal symptom threshold level. "Removing" the single dosage form can include extracting an intravaginal single dosage form, surgically removing a subcutaneous or intramuscular single dosage form, and peeling off a transdermal or buccal single dosage form. In some embodiments, the administration can be discontinued after a pre-determined amount of time, if the pre-determined amount of time is sufficiently long enough such that the release rate of the active agent is at or below a terminal symptom threshold level when the administration is discontinued.

As used herein, "terminal symptom threshold level" refers to a release rate of an active agent to a subject at or below which the administration can be discontinued without inducing a symptom associated with an abrupt reduction in an endogenous or exogenous chemical in the subject. In some embodiments, a terminal symptom threshold level refers to a release rate of the active agent in which removal of the single dosage form from the subject will not cause significant adverse effects. In some embodiments, a terminal symptom threshold level refers to a release rate of the active agent in which abrupt disruption or cessation of the administration will not result in a symptom in the subject.

For example, a terminal symptom threshold level for reducing a symptom associated with menopause can include administering an equivalent conjugated estrogen (PREMARIN® at a release rate of about 0.1 mg/day to about 2.0 mg/day, a release rate of about 0.2 mg/day to about 1.0 mg/day, or a release rate of about 03 mg/day to about 0.8 mg/day.

For example, a terminal symptom threshold level for reducing a symptom associated with an addiction to nicotine can include administering nicotine at a release rate of about 5.0 mg/day to about 20 mg/day, a release rate of about 2.5 mg/day about 10 mg/day, or a release rate of about 0.1 mg/day to about 3.0 mg/day. For example, a terminal symptom threshold level for reducing a symptom associated with an addiction to heroin, or another opiate substance, can include administering methadone at a release rate of about 1.0 mg/day to about 100 mg/day, or a release rate of about 20 mg/day to about 40 mg/day.

While not being bound by any particular theory, reducing a symptom by a method of the present invention is achieved by administering an amount of an active agent from a single dosage form, wherein the release rate of the active agent from the single dosage form is above the symptom threshold level, and wherein the release rate of the active agent tapers throughout the administration. By administering the active agent at a tapering release rate, the subject can respond to the administration by requiring a decreasing amount of the active agent to reduce the symptom. Thus, the symptom threshold level can also decrease throughout the administration. While not being bound by any particular theory, because the administration of the active agent tapers over time, there is no inducement or reoccurrence of the symptom in the subject that can result from a break, interruption, abrupt reduction, or discontinuity in the administration. In some embodiments, the release rate of the active agent tapers until discontinuing the administration will not result in a reduction of a symptom associated with an abrupt reduction in an endogenous or exogenous chemical in a subject.

The methods of the present invention can be used in conjunction with other methods and dosage forms. For example, administering an active agent at a constant dosage regimen results in a discontinuity at the conclusion of the regimen. Additionally administering an active agent by a step-down dosage regimen results in discontinuous administering during and at the conclusion of the regimen, which can result in a reoccurrence of the condition, or the symptoms thereof, thereby diminishing the effectiveness of the regimen. Thus, the methods of the present invention can be administered at the conclusion of either a constant dosage or step-down dosage regimen to improve the effectiveness of these regimens in treating the condition, and preventing a reoccurrence of a condition or the symptoms thereof.

The intravaginal, transdermal, buccal, subcutaneous, or intramuscular dosage form for use with the present invention can comprise an excipient. An "excipient" refers to a pharmacologically inert substance that enables the active agent to be released from the single dosage form at a tapering rate. In some embodiments, an excipient can be contained in, or comprise, a bio-adhesive layer of a transdermal or buccal dosage form. Suitable excipients include solubilizing agents, permeation enhancers and penetration enhancers.

In some embodiments, the present invention is directed to a single dosage form for intravaginally, transdermally, buccally, subcutaneously, or intramuscularly administering an active agent to a subject to reduce a symptom associated with an abrupt reduction in an endogenous or exogenous chemical in a subject, the dosage form comprising a carrier and an active agent. As used herein, "a carrier" refers to a material that is miscible with that active agent, a material in which the active agent is soluble, or a solid material that can be uniformly blended with the active agent, (e.g., polymeric materials such as polyacrylic and poly(alkyl)acrylic acids, elastomeric polymers, hydrophilic and hydrophobic cellulose derivatives, etc.) A carrier can comprise anyone of a polymer, an emulsion, a plaster, a gel, an epoxy, an oil, a surfactant, and combinations thereof, that can be used to contain or solubilize an active agent. In some embodiments, the carrier can comprise a matrix, reservoir, film, ring, laminar or multilaminate structure, plaster, or gel useful for containing or storing, and then releasing an active agent.

The single intravaginal, transdermal, buccal, or subcutaneous dosage forms of the present invention for use with the methods of the present invention can further comprise one or more rate-controlling layers, membranes, or films that surround the active agent or that the active agent must pass through to be released from the single dosage form. A rate-controlling layer can control the rate of release of the active agent from the single dosage form, and ensure that the rate of release tapers over an extended period of time.

The single dosage forms for use with the present methods of the invention release an active agent for a period of time to reduce a symptom associated with an abrupt reduction in an endogenous or exogenous chemical in a subject. The period of time for which a single dosage form is administered can depend on the method by which the dosage form is administered (i.e., intravaginally, transdermally, buccally, intramuscularly, or subcutaneously). In some embodiments, dosage forms of the present invention are capable of releasing an active agent for extended periods of time. The period of time a dosage form is administered can vary depending on the method of administering the dosage form, the type of an active agent, the amount of an active agent, and the symptom that is being reduced.

in some embodiments, single dosage forms for use with the present invention intravaginally administer an active agent to a subject a release rate that tapers for about one week to about one year, or greater than one year, up to about four years. In some embodiments, single dosage forms for use with the present invention intravaginally administer an active agent to a subject at a release rate that tapers for about one week to about six months. In some embodiments, single dosage forms for use with the present invention intravaginally administer an active agent to a subject at a release rate that tapers for about one week to about three months. In some embodiments, single dosage forms for use with the present invention intravaginally administer an active agent to a subject at a release rate that tapers for about one week to about one month. In some embodiments, single dosage forms for use with the present invention transdermally or buccally administer an active agent to a subject at a release rate that tapers for about three days to about ten days. In some embodiments, single dosage forms for use with the present invention transdermally or buccally administer an active agent to a subject at a release rate that tapers for about four days to about ten days, in some embodiments, single dosage forms for use with the present invention transdermally or buccally administer an active agent to a subject at a release rate that tapers for about five days to about ten days.

In some embodiments, single dosage forms for use with the present invention subcutaneously or intramuscularly administer an active agent to a subject for a release rate that tapers for about one month to about one year. In some embodiments, single dosage forms for use with the present invention subcutaneously or intramuscularly administer an active agent to a subject at for a release rate that tapers for about one month to about three months. In some embodiments, single dosage forms for use with the present invention subcutaneously or intramuscularly administer an active agent to a subject for a release rate that tapers for about one month to about six months. In some embodiments, single dosage forms for use with the present invention subcutaneously or intramuscularly administer an active agent to a subject for a release rate that tapers for about one year or longer.

In some embodiments, the active agent can be passively released from the single dosage form. As used herein, "passively released" refers to release of the active agent through non-mechanical means. In some embodiments, the active agent is passively released from the single dosage form through, but not limited to, diffusion, secretion, or osmosis. In some embodiments, the active agent is actively released from the single dosage form. As used herein, "actively released" refers to the release of the active agent through mechanical means. In some embodiments, the active agent is actively released from the single dosage form through, but not limited to, osmotic pumps, electrically driven pumps, or piezoelectric elements that release active agents in response to an applied current.

The total amount of an active agent administered to a subject can be varied, but must be sufficient to administer the active agent at the desired rates throughout the administration period. The amount of the active agent to be administered to a subject can be determined by the nature of the symptom and/or the characteristics of the subject, e.g., weight, age, health, etc. In some embodiments the amount of the active agent administered to a subject can be determined by a person of skill in the art. One of skill in the art can perform pharmacokinetic studies and use the results thereof to adjust the dosage amount to a suitable level, or determine an appropriate dosage amount based on systematically varying the dosage amount administered to a subject and monitoring the symptoms of the subject after the administration. Appropriate animal studies can be performed to determine an appropriate dosage amount. As used herein, "one of skill in the art" includes, for example, a physician, a physician's assistant, a nurse practitioner, a pharmacist, pharmacologist, phamiacokineticist and a customer service representative.

The present invention is directed to a kit, or "therapeutic package," comprising a single dosage form and a label comprising directions for the use of the package for reducing a symptom associated with an abrupt reduction in an endogenous or exogenous chemical in a subject. In some embodiments, a therapeutic package can comprise a cardboard or paper package with printed instructions. A kit or therapeutic package can contain a single dosage form. In some embodiments, a kit or therapeutic package can contain a single dosage form of a given strength. A "label" or "printed instructions" can be in a form prescribed by a governmental agency regulating the manufacture, use or sale of pharmaceuticals or biological products, which notice reflects approval by the agency of the manufacture, use or sale for human administration to reduce a symptom. The kit can further comprise printed matter, which, e.g., provides information on the use of the single dosage form to reduce a symptom, or a pre-recorded media device which, e.g., provides information on the use of the single dosage form to reduce a symptom. "Printed matter" can be, for example, one of a book, booklet, brochure or leaflet. The printed matter can describe the use of the single dosage form of the present invention to reduce a symptom associated with an abrupt reduction in an endogenous or exogenous chemical in a subject. Possible formats included, but are not limited to, a bullet point list, a list of frequently asked questions (FAQ) or a chart. Additionally, the information to be imparted can be illustrated in non-textual terms using pictures, graphics or other symbols.

All of the various embodiments or options described herein can be combined in any and all variations.

The following examples are further illustrative of the present invention, but are not to be construed to limit the scope of the present invention.

Example 1

Preparation of an Estradiol Vaginal Ring

A vaginal ring containing estradiol, silicone polymers and barium sulfate is prepared according to methods known in the art. See physician's leaflet for ESTRING® (estradiol vaginal ring, Pfizer, Inc., New York, N.Y., August 2008). The vaginal ring demonstrates release kinetics for an estradiol over a period of time. A plot of the release rate will show a release rate of about 0.3 µg/hour one hour after administration. The vaginal ring continues to release estradiol from the ring over the course of about nine months. The release rate of estradiol from the ring tapers, without abrupt changes, until the release rate is at or below a terminal symptom threshold level in subject.

Example 2

Reduction of Symptoms Associated with Menopause

A female subject suffering from symptoms associated with menopause, e.g., hot flashes, is administered a vaginal ring comprising ethinyl estradiol as described in Example 1. Upon administration of the ethinyl estradiol vaginal ring to the subject, ethinyl estradiol is released from the vaginal ring at a rate sufficient to reduce the occurrence of hot flashes in the subject, wherein the release rate of ethinyl estradiol tapers over about 1 year. After one year, the release rate of ethinyl estradiol has tapered to, or below, a terminal symptom threshold level. The vaginal ring is then removed from the subject without inducement or reoccurrence of hot flashes in the subject.

Example 3

Preparation of a Vaginal Ring Comprising Methadone

An intravaginal ring is prepared as described in U.S. patent application Ser. No. 12/539,568, except methadone is placed in the vaginal ring instead of estrogen and progestin. The resulting intravaginal ring has an outer diameter of about 40 mm to 60 mm, an inner diameter of 10 mm to 40 mm, and a cross-sectional diameter of 5 mm to 8 mm. The support of the intravaginal ring has a cross-sectional diameter of 2 mm to 4 mm.

Example 4

Reduction of Symptoms Associated with Heroin Addiction

A female subject suffering from symptoms associated with heroin addiction is administered a vaginal ring comprising methadone as described in Example 3. Upon administration of the methadone vaginal ring to the subject, methadone is released from the vaginal ring at a rate sufficient to reduce the symptoms associated with heroin, wherein the release rate of methadone tapers over about 30 days. After about 30 days, the release rate of methadone has tapered to, or below, a terminal symptom threshold level. The methadone vaginal ring is then removed from the subject without inducement or reoccurrence of symptoms associated with heroin addiction in the subject.

Example 5

Preparation of a Vaginal Ring Comprising Nicotine

A vaginal ring comprising trifluoropropylmethyl/dimethyl siloxane is made as described in U.S. Pat. No. 6,436,428, except nicotine is added as an active agent instead of oxybutynin. The ring is given 24 hours at ambient conditions to allow the ring to fully cure, resulting in a vaginal ring comprising nicotine.

Example 6

Reduction of Symptoms Associated with Nicotine Addiction

A female subject suffering from symptoms associated with nicotine addiction is administered a vaginal ring as described in Example 5. Upon administration of the nicotine vaginal ring to the subject, nicotine is released from the vaginal ring at a rate sufficient to reduce the symptoms associated with nicotine addiction, wherein the release rate of nicotine tapers over about six months. After about six months, the release rate of nicotine has tapered to, or below, a terminal symptom threshold level. The nicotine vaginal ring is then removed from the subject without inducement or reoccurrence of the symptoms associated with nicotine addiction in the subject.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated, by reference herein, including all data, tables, figures, and text presented in the cited documents.

What is claimed is:

1. A method of reducing a symptom associated with an abrupt reduction in an endogenous or exogenous chemical in a subject, the method comprising:
   (a) vaginally administering to the subject a single administration of a single dosage form comprising an active agent, wherein the release rate of the active agent from the single dosage form tapers throughout the administration; and
   (b) removing the single dosage form from the subject after the release rate of the active agent is at or below a terminal symptom threshold level.

2. The method of claim 1, wherein the single dosage form is administered to the subject for about one week to about one year.

3. The method of claim 1, wherein the single dosage form is administered to the subject for about at least three days.

4. The method of claim 1, wherein the symptom is associated with menopause.

5. The method of claim 1, wherein the active agent is a hormone.

6. The method of claim 5, wherein the hormone is selected from the group consisting of an estrogenic compound, a progestinic compound, an androgenic compound, a corticosteroid, and combinations thereof.

7. The method of claim 1, wherein the symptom is associated with withdrawal due to a cessation in the administration of an endogenous or exogenous chemical to the subject.

8. The method of any one of claim 7, wherein the active agent is selected from the group consisting of a stimulant, a beta-blocker, an opioid, an opioid antagonist, a benzodiazepine, a barbiturate, and a selective serotonin reuptake inhibitor (SSRI).

9. The method of claim 1, wherein the symptom is associated with an addiction to an exogenous chemical.

10. The method of claim 9, wherein the active agent is selected from the group consisting of nicotine, caffeine, and methadone.

11. The method of claim 1, wherein the single dosage form is selected from the group consisting of an intravaginal ring, an intrauterine dosage form, and a vaginal pessary.

12. The method of claim 1, wherein the single dosage form is an intravaginal ring.

13. The method of claim 1, wherein the dosage form is an implant.

14. The method of claim 1, wherein the release rate of the active agent tapers linearly throughout the administration.

15. The method of claim 1, wherein the release rate of the active agent tapers biphasically throughout the administration.

16. The method of claim 1, wherein the release rate of the active agent tapers first order exponentially throughout the administration.

17. The method of claim 1, wherein the active agent is passively released from the single dosage form.

18. The method of claim 1, wherein the active agent is actively released from the single dosage form.

19. A therapeutic package comprising:
   (a) the single dosage form of claim 1; and
   (b) a label comprising directions for use of the single dosage form for reducing a symptom associated with the abrupt reduction in an endogenous or exogenous chemical in a subject.

* * * * *